(12) United States Patent
Raghuprasad (10) Patent No.: US 8,043,214 B2
(45) Date of Patent: Oct. 25, 2011

(54) NEURO-AID

(76) Inventor: Puthalath Koroth Raghuprasad, Odessa, TX (US)

( * ) Notice: Subject to any disclaimer, the term of this patent is extended or adjusted under 35 U.S.C. 154(b) by 330 days.

(21) Appl. No.: 12/398,338

(22) Filed: Mar. 5, 2009

(65) Prior Publication Data

US 2010/0228098 A1 Sep. 9, 2010

(51) Int. Cl.
*A61B 5/00* (2006.01)
*A61B 3/12* (2006.01)
*A61B 3/02* (2006.01)

(52) U.S. Cl. ........ 600/300; 351/214; 351/239; 600/558; 600/553

(58) Field of Classification Search .......... 600/300–301, 600/553, 557, 558; 351/200–247
See application file for complete search history.

(56) References Cited

U.S. PATENT DOCUMENTS

| | | | | |
|---|---|---|---|---|
| 1,269,820 A | * | 6/1918 | Karatsu | 600/557 |
| 2,315,160 A | | 3/1943 | Newstedt | |
| 2,328,700 A | | 9/1943 | Wiltberger | |
| 2,330,882 A | * | 10/1943 | Gray | 600/553 |
| 2,532,093 A | * | 11/1950 | Field et al. | 600/553 |
| 2,678,692 A | | 5/1954 | Ranseen | |
| 2,704,539 A | | 3/1955 | Fisher | |
| 2,908,268 A | | 10/1959 | Guest | |
| 3,185,146 A | * | 5/1965 | Leopoldi | 600/553 |
| 3,344,781 A | * | 10/1967 | Allen | 84/457 |
| 3,515,125 A | * | 6/1970 | Ruskin | 600/553 |
| 3,852,432 A | * | 12/1974 | Henkin | 424/643 |
| 4,166,452 A | | 9/1979 | Generales | |
| 4,953,970 A | * | 9/1990 | Telchin | 351/223 |
| 5,233,988 A | | 8/1993 | Raghuprasad | |
| 5,568,209 A | * | 10/1996 | Priester et al. | 351/243 |
| 6,132,830 A | | 10/2000 | O'Halloran | |

(Continued)

FOREIGN PATENT DOCUMENTS

DE 29518562 11/1995

(Continued)

OTHER PUBLICATIONS

NPL_Teststrips.pdf p. 1-2.*

*Primary Examiner* — Henry M Johnson, III
*Assistant Examiner* — Marie Archer
(74) *Attorney, Agent, or Firm* — David L King (57) ABSTRACT

An improved neurological testing apparatus 10 for examining a person's neurological system has a body housing 12, one or more separate specific taste testing substances 20, one or more separate specific smell testing substances 30, one or more vision charts 40, 42 and a light source 50. The body housing 12 includes a front surface 12A, a rear surface 12B, an upper end 14, a bottom end 16 and an interior chamber 18 for holding a battery 100. The separate specific taste testing substances 20 are attached to the front or rear surfaces. The separate specific smell testing substances 30 are attached to either the front or rear surface. The vision charts 40, 42 lie on one of the front or rear surfaces opposite the smell or taste testing substances 20, 30. The light source assembly 50 is mounted in the body structure 12 and includes a light 50A connected to a battery 100 via an on/off switch 60 located in the body 12, wherein said light source 50 is used to analyze pupillary reflex as seen through an eye examination lens 4 located directly above the light 50A and for examining the fundus of the eye (retina).

14 Claims, 6 Drawing Sheets

U.S. PATENT DOCUMENTS

| | | | |
|---|---|---|---|
| 6,406,436 B1 * | 6/2002 | Schiffman | 600/557 |
| 6,896,656 B2 | 5/2005 | Krass | |
| 6,957,038 B1 | 10/2005 | Gartner | |
| 7,396,128 B2 | 7/2008 | Feher | |
| 7,857,450 B1 * | 12/2010 | Hofeldt | 351/243 |
| 2007/0077204 A1 | 4/2007 | Devanand | |
| 2010/0106049 A1 * | 4/2010 | Boslough et al. | 600/553 |

FOREIGN PATENT DOCUMENTS

| | | |
|---|---|---|
| GB | 2384989 | 11/2001 |

* cited by examiner

NEURO-AID

FIELD OF THE INVENTION

This invention relates to a device for examining the neurological system, in particular the cranial nerve.

BACKGROUND OF THE INVENTION

The neurological examination is accomplished by examining in succession, the higher functions by testing memory, intelligence, orientation in time, place and person, and speech, the cranial nerves, the motor and sensory systems, cerebellar functions and the reflexes. In practice, those skilled in the art of testing the nervous system have been required to carry numerous separate testing devices. This variety of testing devices carried by the clinician is costly and cumbersome and if not done in a sequential methodology oftentimes the testing of certain sensory aspects can be missed.

The present invention is designed with the express intent of providing in one small device many of the essential ingredients for a thorough neurological examination. The device which can be carried in a lab coat pocket or shirt pocket, is made in a simple and relatively inexpensive fashion so that the device can either be used as a disposable device or as a low cost tool by the clinician.

In U.S. Pat. No. 5,233,988 a neuro-aid satisfying some of the above requirements was granted a patent on Aug. 10, 1993. This original neuro-aid device provided a portable, inexpensive tool which the clinician could use to examine a patient for neurological responses. While being an efficient device for neurological examinations it lacked several features which are considered to be essential in proper neurological examinations.

The present invention is an improved neuro-aid device which provides low cost solutions to neurological examinations while providing additional capabilities. The improved device adds features that will enable the clinician to examine the fundus (retina) and sensitivity to light as well as providing an improved aseptic method of conducting touch responses using a sterile, detachable pin system. Provisions have also been made for metric scale for measuring the size of pupil and for carrying charts and/or tables within the device.

It is currently recognized that in many athletic sports and other activities head injuries often occur. These head injuries can be rated from minor to severe. Commonly referred to as concussions or mild traumatic brain injuries (MTBI), these are the most common and least serious of this type of traumatic brain injury. These concussions involve a transient loss of mental functions that can be caused by acceleration or deceleration forces or by a direct blow. Concussions are generally not associated with penetrating head injuries. Patients with concussions may act confused for example repeatedly asking the same question or forgetting where they are. Patients may have focal neurological deficits, signs that a specific part of the brain is not working correctly. While such trauma are considered mild generally, the brain is adapted in such a way that after a mild concussion, a repeated secondary impact on the brain can lead to serious and permanent brain damage and potentially death. As a result in such sports as football, head injuries are reviewed by a trainer immediately and certain sensory responses are tested to see if the player has been injured seriously enough that he should no longer play. It is not uncommon for a player who has had a head injury to return to play within a week and upon receiving a secondary head injury, of dying. As a result many high school and college programs by state law are required to have medically trained physical trainers onsite to look for these types of head injuries. One of the best ways of indicating whether a person has received a concussion is an examination of the eyes. If the eyes show aberrant movement or one pupil is dilated more than the other or if the eyes fail to respond to light sensitivity may be strong indications that the player has had a concussion. As a result it is now normal practice to remove such players from further contact. It is accordingly very important that these trainers have tools that will enable eye reflexes to be easily examined. Checking the peripheral vision was available on the prior art device, however, this device was lacking in that light sensitivity and fundus could not be examined. Accordingly, a need to improve the device incorporating such a feature was determined necessary.

In addition, in checking an injured person's response to touch to determine if any nerve damage had occurred to any limbs or any portion of the nervous system has been essential in these neurological examinations. The prior art device of U.S. Pat. No. 5,233,988 provided an integrally molded sharp point at one end of the device which could be used to poke into the patient to determine if the sense of pain was felt in the location where the device was pushed. This exposed the person conducting the test and the subsequent patient's to the increased risk of contracting blood transmitted diseases from the person being examined. As such the entire device typically had to be thrown away. It was determined that had this touch test been one that could be provided by a removable needle or pin, the device could then be used on multiple patients without the risk of either transmitting blood-borne diseases. These and other beneficial improvements have been provided in the improved inventive device as described below.

SUMMARY OF THE INVENTION

An improved neurological testing apparatus for analyzing a persons sense receptors has a body housing, one or more separate specific taste testing substances, one or more separate specific smell testing substances, one or more vision charts, other charts/tables and a light source assembly. The body housing includes a front surface, a rear surface, an upper end, a bottom end and an interior chamber. The separate specific taste testing substances are attached to the front or rear surfaces. The separate specific smell testing substances are attached to either the front or rear surface. The vision charts lie on one of the front or rear surfaces opposite the smell or taste testing substances. The light source assembly is mounted in the interior chamber of the body housing. The light source assembly includes a light or LED lamp connected to a battery via an on/off switch contained in said body, wherein said light source assembly is used to analyze pupillary reflex. An eye examination lens for observing the interior of the patient's eyes is provided. The lens is aligned with and preferably located above the light. The lens extends from the rear surface and is open to an opening or hole in the front surface of the body housing. A mirror or prism redirects the light transmitting it through the opening in direct alignment with the lens.

The improved neurological testing apparatus at one end has an integral disk having a red side and an opposite white side to use in field of vision determination and at an end opposite the disk the body housing includes a cavity or slot for holding instruction cards or patient cards.

The improved neurological testing apparatus further has one or more sterile needle holders formed or otherwise molded into the body housing for receiving and storing one or more sheathed sterile needles or pins, the sterile needle or pin being configured to be removably detached from the needle holder for testing for pain sensation. After the test for nerve damage is completed the used needle can be re-sheathed to be appropriately discarded. The improved neurological testing apparatus further may have one or more swab holders formed or otherwise molded into the body housing for holding and storing one or more cotton tipped swabs. The cotton tipped swabs are removably detachable from the swab holder. After being used, the swabs can simply be discarded.

The one or more separate specific smell testing substances are located on one side of the body housing and spaced from each other. Each separate specific smell testing substance is preferably formed in stacked layers covered or sealed by a re-sealable cover.

Similarly, the one or more taste testing substances are spaced from each other and located on one side of the body housing. Each taste testing substance is preferably formed in stacked layers each stack of layers being covered or sealed by re-sealable covers.

In a preferred embodiment, the specific taste testing substance can include at least two or more taste testing substances selected from a group of sweet, sour, salty or bitter. The separate specific taste and smell testing substances all lie in cavities on the same surface, preferably the rear surface of the body housing, with the vision charts lying on the opposite front surface.

The layers or strips of the separate and specific taste and smell test substances can have the test substance attached to or adhered to the underside of the strip or the top side of a strip. The outermost strip or layer is exposed upon opening of a sealable cover or alternatively the taste strips can be entirely edible.

These features enable the device to be safely used on a plurality of different patients without the risk of transmitting diseases from prior patients. Accordingly the device, while being extremely low in cost, provides the added advantage of being aseptically usable on multiple patients by simply replacing the used sterile sheathed needles or pins and used cotton tipped swabs and replacing them with new ones as needed.

The device preferably is also designed to enable replacement of the battery and addition of replacement taste and smell test peel-off packets which can be adhesively affixed to the body housing in their predetermined location which can be a raised plateau or recessed cavity depending on the design of the body housing.

BRIEF DESCRIPTION OF THE DRAWINGS

The invention will be described by way of example and with reference to the accompanying drawings in which:

FIG. 2 is a perspective view showing the rear surface of a neuro-aid testing apparatus of FIG. 1, the device as shown has one sterile needle or probe tip removed from a recessed sterile needle or probe tip holder formed or otherwise molded as a depression or cavity into the body housing of the apparatus. The needle or probe tip is sheathed in a covering and snap set into the holder. Similarly, one cotton tipped swab is shown removed from a swab holder. Additionally a plurality of recessed storing cavities for holding various sensor receptors testing substances is shown. In a first cavity the test substance layers are shown removed from the cavity as is a covering that seals and encloses the testing substances. An eye examination lens is also shown removed from a lens mounting hole in the body housing.

FIGS. 13A, 13B and 13C show cross sectional views of the needle or probe tip holder cavity with the needle or probe tip in place. In FIG. 13A the needle or probe tip is in its normally stowed position. In FIG. 13B the needle or probe tip is shown being tilted into a larger cavity portion of the needle or probe tip holder such that the front end of the needle or probe tip is released from a retaining protrusion on the frontal end of the sheathed needle or probe tip exposing the front end of the needle or probe tip to be lifted thereafter as shown in FIG. 13C removing the needle or probe tip from retention by the protrusion.

DETAILED DESCRIPTION OF THE INVENTION

Figure 1:
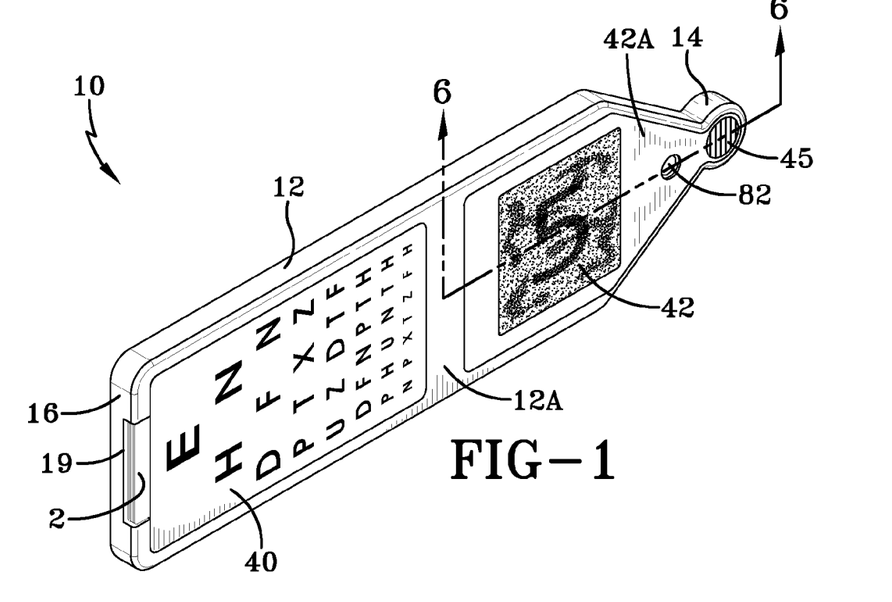
FIG. 1 is a perspective view of the front surface of the neuro-aid testing apparatus made in accordance with the present invention.
Figure 2:
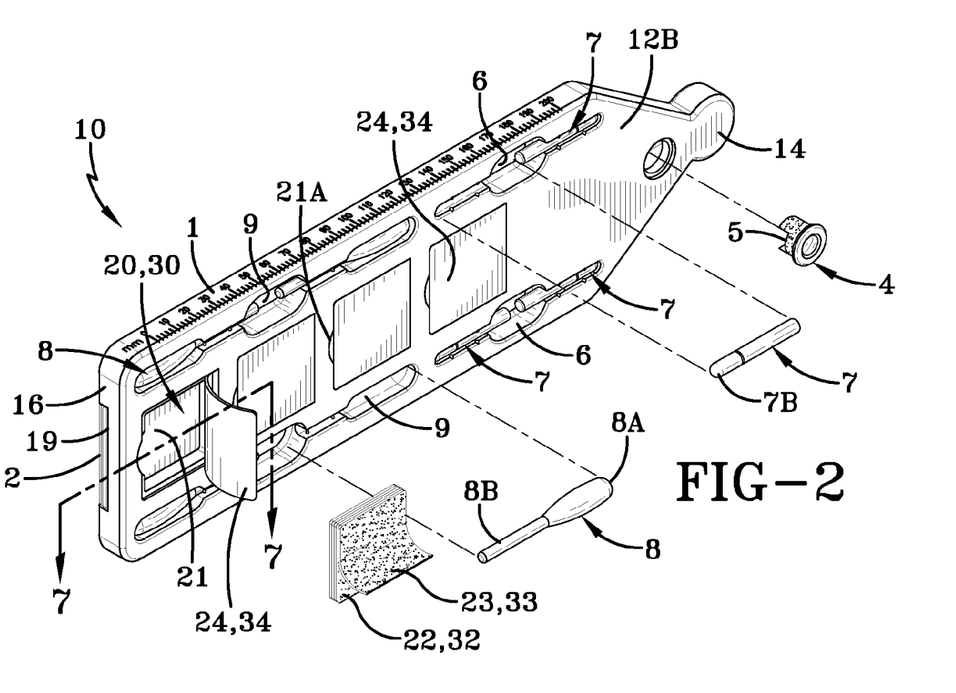
Figure 3:
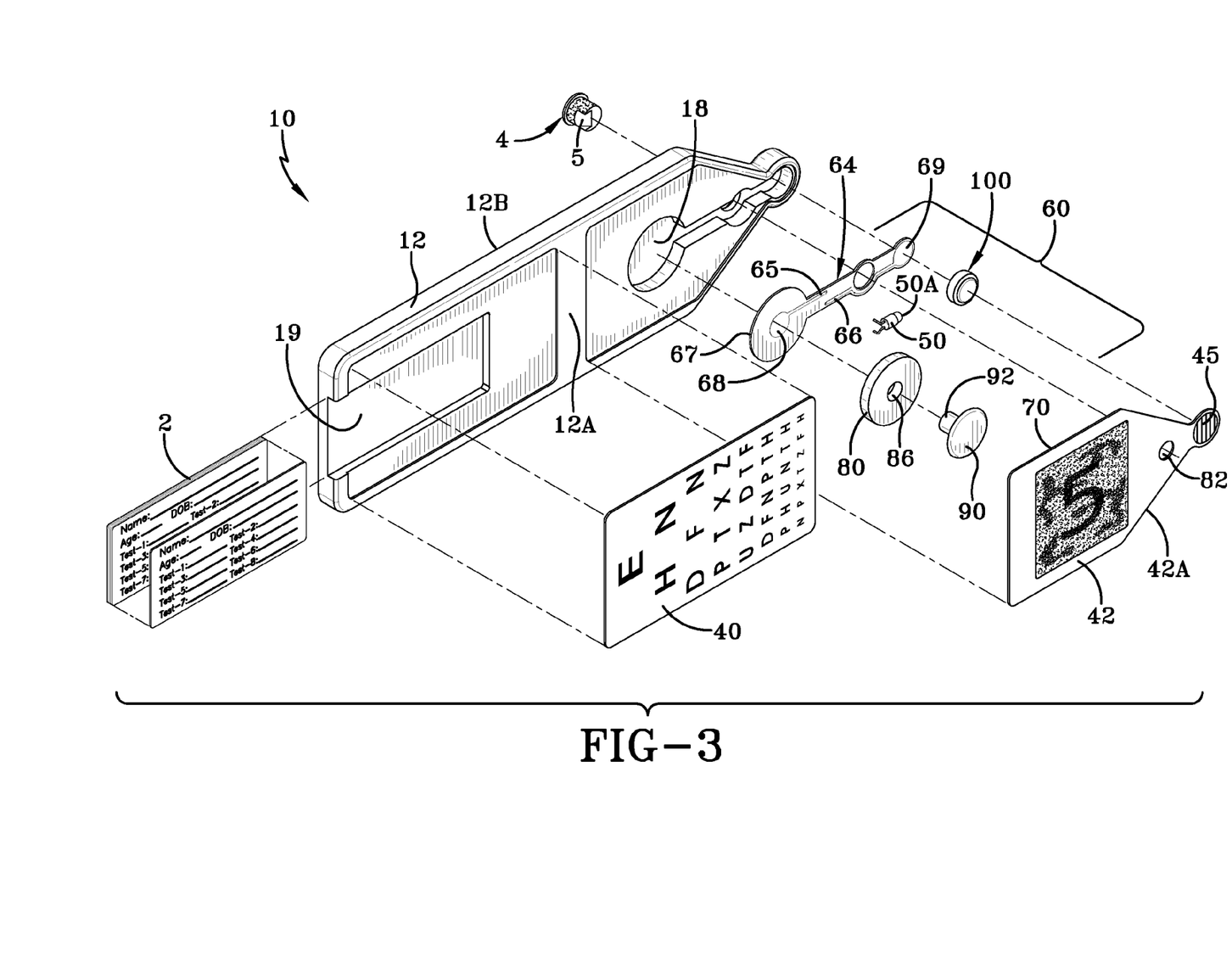
FIG. 3 is a frontal perspective exploded view of the apparatus showing a Snellen eye chart label for attachment on the lower front portion of the body housing and an exploded view of a color blindness testing label covering a light source assembly including a light and light switch mechanism with batteries and a lens on an upper portion of the body housing. Instruction or patient information cards are also shown which are held in a recessed slot formed under the Snellen eye chart label.
Figure 4:
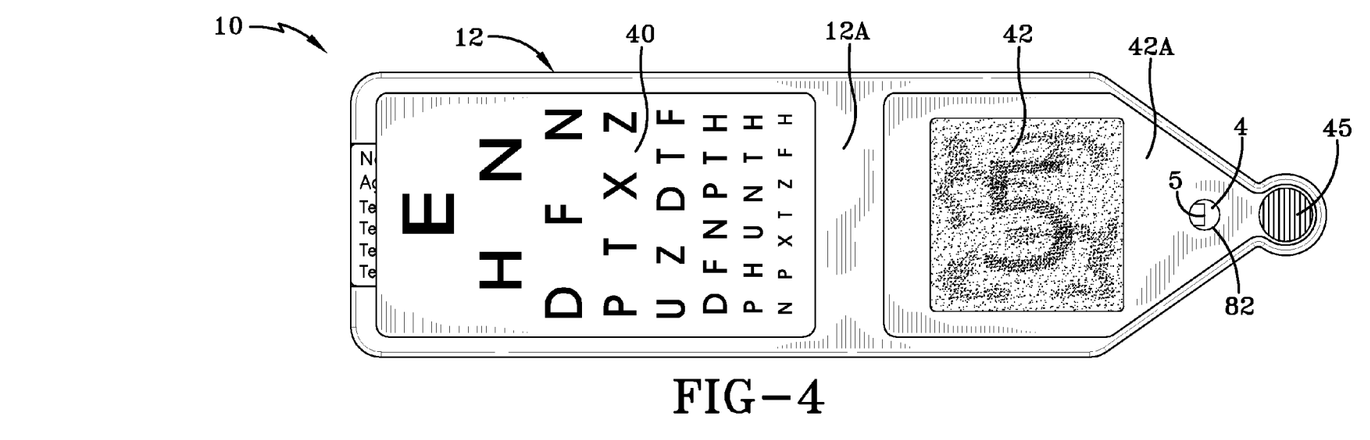
FIG. 4 is a frontal plan view of the apparatus of FIG. 1.
Figure 5:
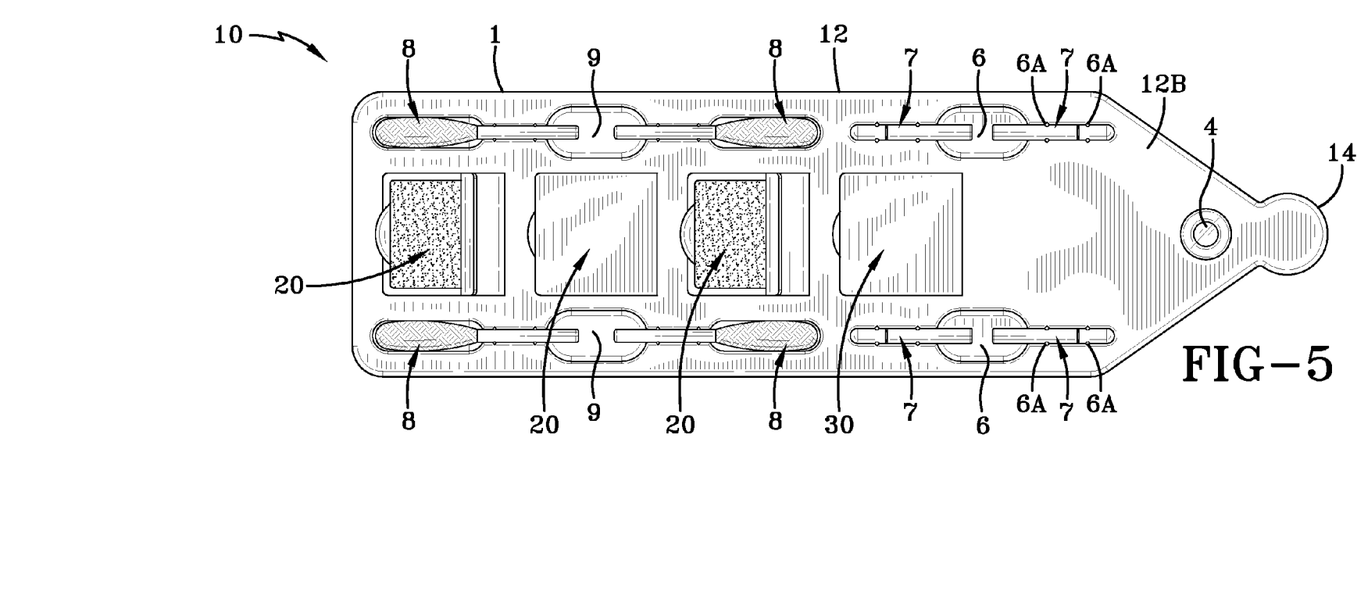
FIG. 5 is a rear view of the apparatus of FIG. 4.

The figures of the drawings disclose an improved neurological testing apparatus 10 for analyzing a person's sense receptors. With reference to FIGS. 1, 2 and 3, the improved neurological testing apparatus 10 has a body housing 12, one or more separate specific taste testing substances 20, one or more separate specific smell testing substances 30, one or more vision charts 40, 42 and a light source assembly 50. The body housing 12 provides the basic structure for the device 10 and includes a front surface 12A and rear surface 12B of generally flat planar construction. The body housing 12 has an upper end 14 and a bottom end 16 with an interior chamber 18 for holding the light source assembly 50 including a light 50A, battery 100 and switching mechanism 60 under a color blindness test chart label 42.

Figure 6:
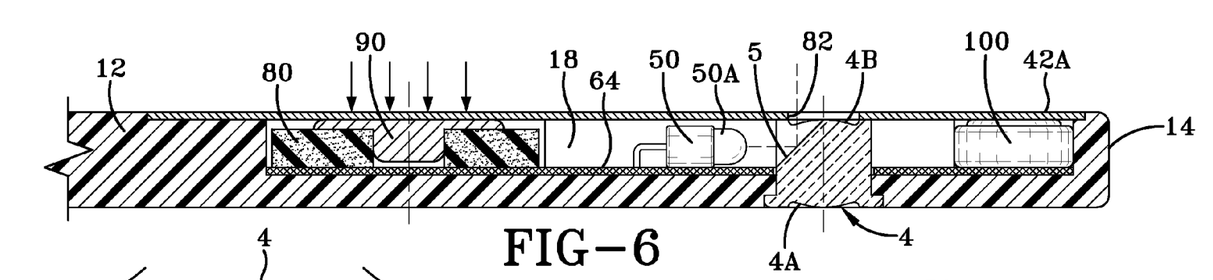
FIG. 6 is a cross-sectional view taken from FIG. 1 showing the light source assembly with a viewing lens, a light, a switch and battery in its stored position in the body housing of the apparatus under the color blindness chart label.
Figure 6A:
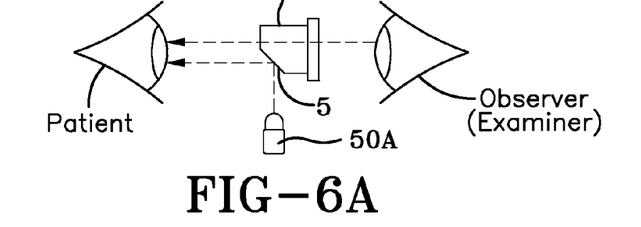
FIG. 6A shows a diagrammatic view of the device being used to check the pupils.
Figure 8:
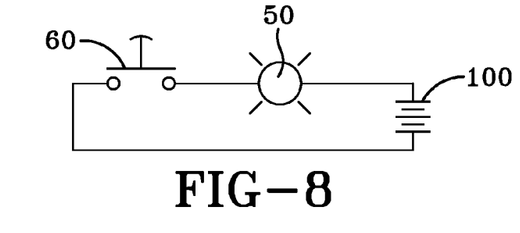
FIG. 8 is an electronic schematic view of the wiring diagram for the light mechanism.

As shown in FIG. 1, the lower portion of the front surface has a Snellen eye chart 40 fixed as a label onto the lower portion of the body housing. Under the label 40 is a recessed slot 19 for holding patient information or test instruction cards 2 or any other useful information such as a concise description of the steps for examining the neurological system or the Glasgow coma scale. Directly above the Snellen chart 40 affixed to the body housing 12 is a color blindness chart 42 formed as part of a label 42A. This label 42A has a circular red dot 45 at an upper end of the label 42A and a hole 82 interposed between the circular red dot 45 and the color blindness chart 42. The hole 82 is provided to allow light to be transmitted from the device. This is better illustrated in FIG. 3 wherein the components of the light switching mechanism 60 is shown. The body housing 12 has a cavity 18 molded into it providing a recess wherein a relatively thin and flat conductive strip 64 is provided to lay in the bottom of the recessed cavity 18 to which a light emitting diode or light 50A is electrically connected to conductive lead material 65, 66 provided on the substrate of the surface of the conductive strip 64. A large diameter circular end portion 67 is provided with a conductive circle portion 68 centrally located under a sponge like or rubber like washer 80 which has a hole 86 which is placed directly above this conductive circle 68. The hole 86 allows a metal or otherwise conductive button 90 to be positioned into the washer hole 86. At the opposite end a round portion 69 of the conductive strip 64 is provided wherein an electric battery 100 is contained. This battery 100 is mounted onto the flat conductive strip 64 such that when the label 42A is assembled with a conductive inner surface 70, the assembled components as shown in cross section in FIG. 6 provides an entire switching mechanism 60. This switching mechanism 60 is activated by depressing the color blindness chart 42 at the number 5. As illustrated in FIG. 6 when the conductive button 90 is moved by compressing against the sponge or rubber like washer 80 an end 92 makes contact with the electrically conductive circle 68 this closes the circuit as shown in FIG. 6, at such a point the circuit is completed and the light 50A will be illuminated. As the light 50A is illuminated, the light passes through the hole 82 in the label 42A as shown. This circuit diagram is further illustrated in FIG. 8. Use of this particular feature enables the person conducting the examination to test the pupillary reflex of a person believed to have some type of neurological injury or symptom. As a result the operator simply presses on the label 42A at the color blindness chart 42, activating a switch 60 illuminating a light 50A and an pupillary reflex response can be tested checking the reflex of the person's pupil and how quickly the eye contracts or dilates with regard to the turning on and off of the light switch 60. To further facilitate the eye examination, a transparent lens 4 is provided as shown in FIGS. 2, 3 and 6. The lens 4 is preferably one piece molded plastic having convex focusing surfaces 4A, 4B. The lens 4 is press fit or glued to the body housing 12. The clear lens 4 preferably has an integral inclined mirror or prism to redirect and deflect the light. As shown, the mirror or prism 5 portion of the lens 4 is preferably positioned to maximize the incident light to the patient and to align the light with the view of the person looking through the lens directly into the patient's pupil, this is as shown diagrammatically in FIG. 6A.

The rounded upper end 14 of the body housing 12 provides a means for testing a patient's peripheral vision. On one side of the upper end 14 the label 42A has a circular portion with a red disk 45 that can be used by moving across the front of the patient to test the peripheral vision of the patient suspected of having a neurological disorder or damage. The red disk 45 as shown is part of the label 42A holding the color blindness chart 42. On the opposite side of the device 10 this circular portion 14 can be colored white and also used to determine a patient's field of vision. The body housing 12 can be made of any particular color if so desired and as such the rear side rounded portion 14 could simply have a label (not shown) of a white color affixed to this circular disk portion 14 if the housing is not made of a white plastic material.

As previously mentioned and as shown in FIGS. 1 and 3, the lower portion of the body housing includes a Snellen eye chart 40. As shown, the Snellen eye chart 40 is illustrated extending along the longitudinal front surface 12A of the body housing 12 and provides numerous eye chart letters of various sizes from which one can test the vision of the patient suspected of having a neurological disorder. As a result, all of the vision testing fundamentally can be conducted using primarily the front surface 12A of the apparatus 10 as illustrated. Under the label 40 in the slot 19 of the housing are stored numerous cards containing patient information or instructions or other useful data.

On the opposite or rearward side 12B of the neurological testing apparatus 10 as shown in FIG. 2 is a plurality of stations containing taste test substances 20 and smell test substances 30 for testing taste and smell. These as shown are four distinct cavities 21 provided on the rear surface 12B of the body housing. These rear cavities 21 include a plurality of taste or smell sensor strips 22, 32 that are located and retained in these cavities 21. Each strip 22, 32 is comprised of a thin layer 23, 33 of material with a specific odor or specific taste. These test stations are separated and each of these layers 23, 33 of strips 22, 32 are embedded in the cavity 21 and sealed in by re-sealable retaining cover 24, 34 as illustrated. The covers 24, 34 can be pried up and there is an access slot 21A enabling one to take their thumb or finger and pry open the cover 24, 34 to expose an underlying layer or strip. These layers or strips 22, 32 can be removed and placed either in front of the patient's nose for a smell test or onto the patient's tongue for a taste test and the person conducting the test can then analyze the patient's ability to distinguish in the case of taste between three distinct tastes preferably sweet, sour or salty. Alternatively as shown one of the cavities 21 can be provided for testing odor which can be provided with a distinctive odor that one could provide such as vanilla, jasmine or rose or otherwise so the patient can identify the odor in which he is smelling. These tests provide information about the cranial nerves number 1, 5 and 9.

For example, the testing of aroma or smell using smell test substance 30 can be conducted such that the odor is reminiscent of one of the following, coffee, roses, clove or cinnamon or mint as previously indicated.

Unlike the prior art neurological testing apparatus of U.S. Pat. No. 5,233,988 the sensory testing substances are provided thin removable strips 22, 32 such that upon lifting the re-sealable cover 24, 34, the strips can be removed and administered to a patient directly. This avoids the possibility of having the patient having either to lick or to smell the substance that have been printed onto or otherwise adhered to the housing 12. This has a tremendous advantage in hygienics and enables the device 10 to be used repeatedly until the strips 22 or 32 are all removed. At which time replacement strips can be provided that would enable the device 10 to be continued to be used.

Figure 9A:
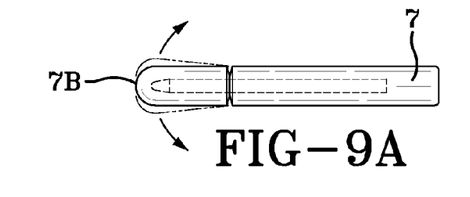
FIG. 9A is a view of a sterile needle or probe tip with the sheath covering showing the forces applied necessary to break the outer sheath covering the tip.
Figure 9B:
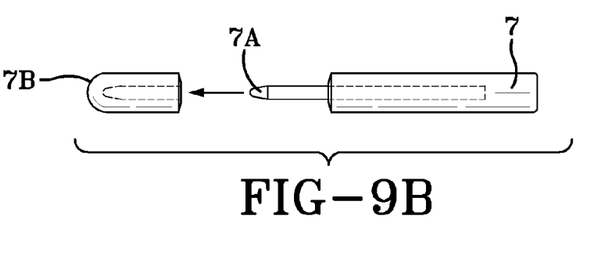
FIG. 9B is a view of the sterile needle or probe tip with the sheath covering removed.
Figure 10A:
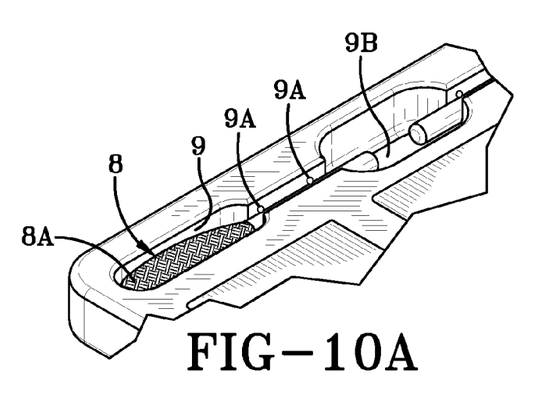
FIG. 10A is a perspective view of the lower portion of the body housing showing a cotton tipped swab inserted into a swab holder cavity formed in the body housing.
Figure 10B:
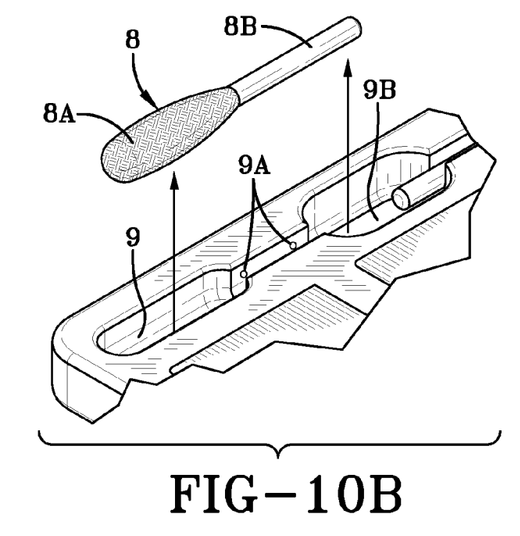
FIG. 10B is taken from FIG. 10A showing a cotton tipped swab removed from a swab holder cavity in the body housing.
Figure 13A:
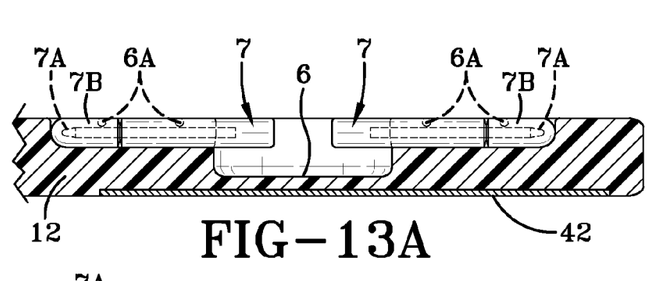
Figures 13B, 13C:
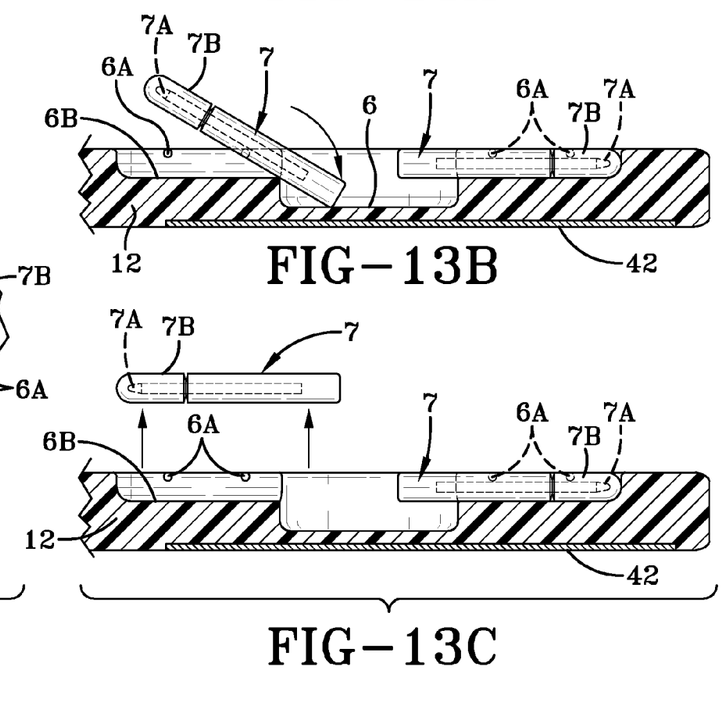

On a portion of the rear surface 12B of the body housing 12 are recessed needle holders 6. These recessed needle holders 6 provide a cavity that retains a pair of needles 7 as shown in FIG. 2. The needles 7 themselves as illustrated in FIGS. 9A and 9B are small pins with a pointed tip 7A as illustrated. Theses tips 7A as shown are covered in a small plastic sheath 7B which can be removed. The opposite end of the tip 7A is encapsulated into preferably a plastic retaining housing 7B. The entire needle 7 is snapped into the recessed holders 6 on the rear side of the body housing 12 for convenient storage. As such the device 10 has no protruding surfaces that can rip a shirt or tear a coat pocket when being carried by a physician or trainer. When desired to test the sensation of pain or nerve sense sensation of a limb or extremity or any other portion of a patients body, the sterile sheathed needle or pin 7 can be removed from its holder 6 on the rearward portion of the body housing 12 by simply pressing on the rearward portion of the needle 7 collapsing it into a larger central cavity 6 as shown in FIGS. 13A, 13B and 13C wherein the needle or pin 7 is tilted upwardly exposing the front of the needle 7 out of the shallow portion 6B wherein the user can then pry the needle 7 out of the cavity 6 wherein the pair of retention protrusions 6A are shown on each side of the needle holder 6. The pairs of retention protrusions 6A snap the needle 7 into a retained position which can be overcome by tilting the needle 7 as illustrated exposing the front end and simply prying the needle out of the retained position. Similarly, once removed, the needle 7 can be used by unsheathing and exposing the tip. Once the tip is exposed, it can be used to press against any portion of a patient to test for nerve damage or touch and feeling sensations. Upon completion of the testing, the needle sheath cover can be reinserted, and the used needle 7 discarded.

By providing a pair of needle holders 6 each holding two needles 7 the device 10 is suitable for repeated use. If the sterile pin 7 should penetrate into the tissue causing any bleeding, the risk of transmission of infection is low. The used needle 7 is always removed and discarded in an aseptic and clean manner such that neither the trainer, physician or tester using the apparatus 10 nor the next patient can be contaminated. This ensures that the device 10 can be used repeatedly wherein sterile needles 7 are provided in packs and enable the user to always have one or more needles 7 stored into the housing 12 of the device 10 for use in pain sensation testing.

The prior art device of U.S. Pat. No. 5,233,988 historically was provided with an integrally molded sharp pyramid shaped protrusion sticking out of the lower end of the device. While this provided a means for quick testing of the pain sensation it was felt that this molded plastic component could be infected with blood of the person being tested. As such, due to the transmission of AIDS or other blood transmitted diseases it is found inappropriate for repeated use. Therefore, the device had to be discarded after one use. The present device 10 eliminates any of these forms of fluid transmitted diseases by providing the patients with removable strips 22, 32 and the needle 7 such that these strips or layers are used only once for each specific patient, discarded and/or absorbed by the patient during the testing procedure and by having removable needles and swabs that are discarded as well leaves the basic apparatus 10 available for repeated use without fear of cross contamination.

Figure 11A:
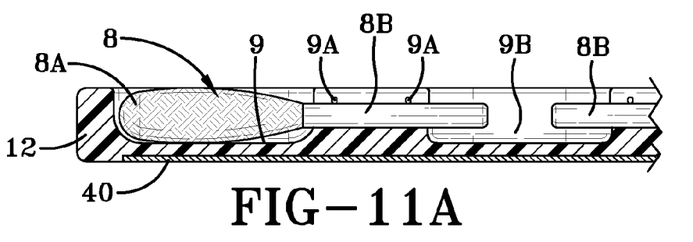
FIG. 11A shows a cotton tipped swab snapped into the swab holder cavity in a cross sectional view.
Figure 11B:
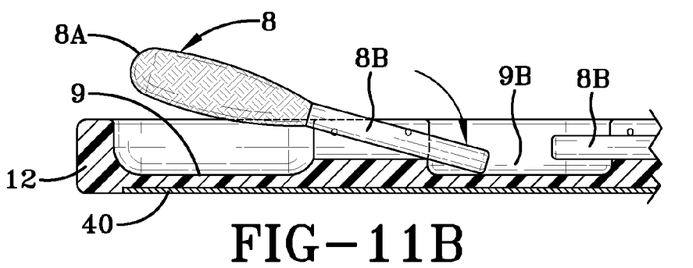
FIG. 11B shows the swab tilted to remove it from the holder cavity in the body housing.
Figure 11C:
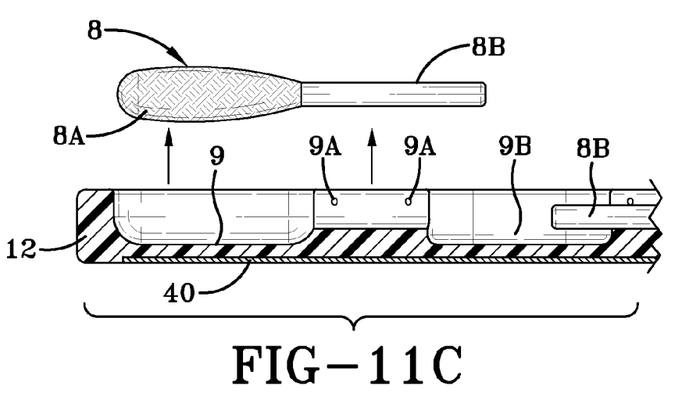
FIG. 11C shows the cotton tipped swab completely removed from the holder cavity molded into the rear surface of the body housing.
Figure 12A:
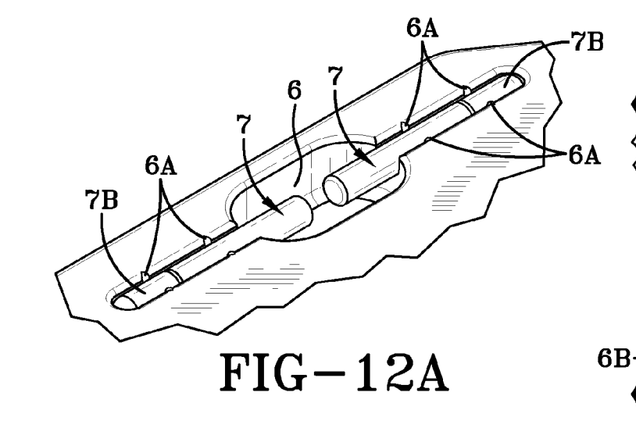
FIG. 12A shows the sterile needle or probe tip in its normally stowed location in the needle or probe tip holder cavity molded into the rear surface of the body housing.
Figure 12B:
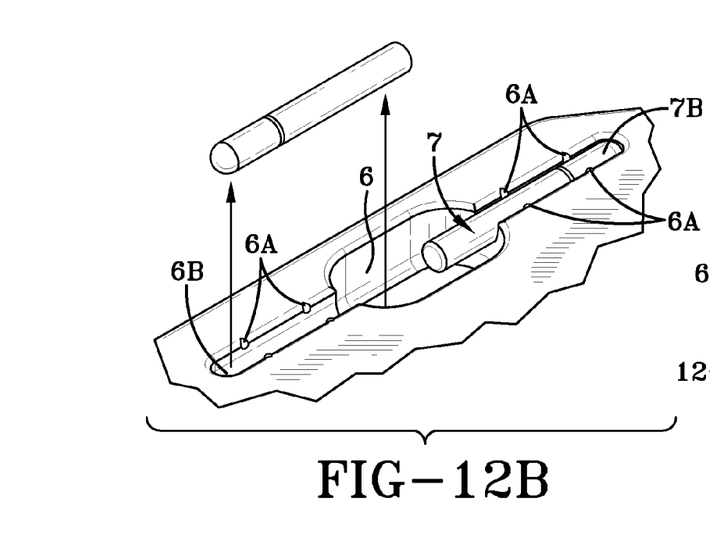
FIG. 12B shows the needle or probe tip removed from the needle holder cavity.

With reference to FIGS. 10A, 10B, 11A, 11B and 11C pairs of cotton-tipped swabs 8 are shown held in recessed holders 9. Each swab 8 has one end covered by an absorbent material or tip 8A of material such as cotton or foam wound on a shaft 8B which can be used for touch sensation. Each swab 8 is held in place by pairs of protrusions 9A. The removal of the swabs 8 is shown in FIGS. 11A, 11B and 11C and is similar to the procedure described earlier for the needle 7. When used carefully, these swabs can be used for testing "corneal reflex" as well.

The present device 10 by providing a battery 100 of a watch type can be used repeatedly for testing the pupils and fundus. The use of a small light emitting diode or lamp 50A to provide a white light to check the pupillary reflexes means that this testing can be conducted numerous times without requiring replacement of the battery 100. As shown, the battery 100 can be removed and replaced by simply peeling the label 45A back and removing the battery 100 at the round end 14 of the housing 12, by replacing the battery 100 the device 10 can be repeatedly used. Furthermore, by providing the taste substances 20 or smell substances 30 in small packs these simply can be replenished as needed. As such, the device 10 while being very low cost and inexpensive, is completely reusable unlike the prior art device which was simply a disposable device that could be used only one time and had to be discarded for hygienic purposes. The present device 10 is intended to be used for multiple and repeated different patients and therefore provides trainers with a very rapid neurological testing apparatus that enables the physician or trainer to observe the patient's condition without requiring to discard the entire unit upon a single use. The testing apparatus 10 as shown has the body housing 12 molded as a single unit. As shown, the slots and recessed cavities are all provided such that a simple open and closed mold can be used without any slides or any other complexities that would require the device to have a more expensive tooling. The tooling itself can be quite simple as illustrated and yet provides multiple functions as shown. The length and height of the testing apparatus body housing 12 can be changed to accommodate any number of stations for taste and smell substances 20, 30 but preferably is of a rectangular configuration made from a thin piece of commercially available self supporting material, such as heavy paper or plastic material that can easily be stamped or cut into the illustrated configuration of the drawings. Alternatively as shown, the device housing 12 could be vacuum formed to provide all of the features as shown similar to plastic packaging and made of a relatively sturdy vacuum formed body housing 12. As such the assembly can be made for extremely low cost if so desired.

Figure 7:
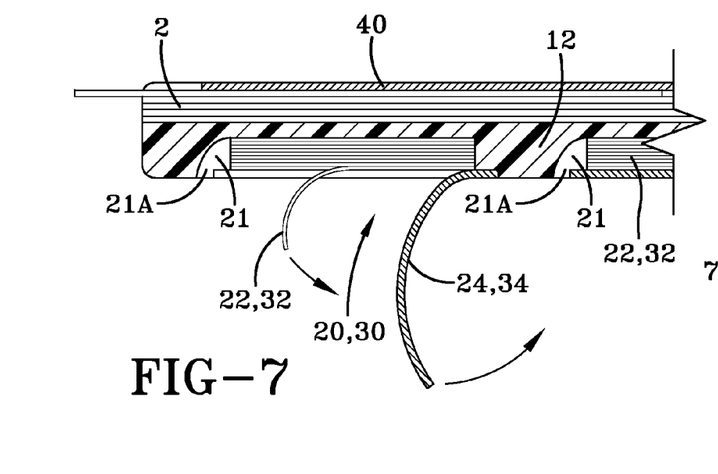
FIG. 7 is a cross sectional view of the apparatus going through an end of the apparatus taken from FIG. 2.

As shown, each of the smell and taste testing substance 20, 30 has the cavity 21 holding the tasting or smelling substance covered by a re-sealable cover 24. This cover preferably is permanently affixed at one end as illustrated in FIGS. 2 and 7. As such, the cover 24 can be peeled up such that a strip 22 or 32 can be removed for conducting a test, once the strip is removed, the cover 24 can then be replaced back into its sealed position by either having the cover snap into the fixed location or by providing an adhesive edge such that the sealing cover provides a hermetic seal to keep the test strips dry and free of contamination.

Additionally, as shown in FIG. 2, a measuring scale 1 is provided on an edge surface of the housing. The measuring scale 1 allows a trainer or physician to measure the pupillary dilation in millimeters. The edge lies between the front and rear surfaces of the body housing and along a longitudinal surface portion of the edge the measuring scale 1 is affixed as a label or is integrally molded into the edge as illustrated.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. An improved neurological testing apparatus for examining a person's neurological system comprising:
    a body housing structure, the body housing structure being a single layer of material including a front surface, a rear surface, an upper end, a bottom end and an interior chamber;
    one or more taste testing substances each sealed by a removable cover and attached to either the front or rear surfaces;
    one or more smell testing substances each sealed by a removable cover and attached to either the front or rear surface;
    one or more recessed needle holders formed or otherwise molded into the body housing structure for receiving and storing one or more sheathed sterile needles, a plurality of sheathed sterile needles being configured to be removably attached to the recessed needle holder for testing for nerve damage and after said test the used needle being re-sheathed for proper disposal;
    one or more vision charts labels affixed to the front surface or the rear surface lying on and covering a portion of one of the front or rear surfaces; and
    a light source assembly mounted in a cavity of the body structure,
    the light source assembly including a light connected to a battery via an on/off switch contained in said body and covered by one of the vision charts label,
    wherein the vision chart label has a hole or aperture to allow light to be emitted from the for the light source assembly,
    wherein said light source assembly is used to analyze pupillary reflex,
    wherein the light is an LED lamp and the battery is a small flat round disk watch type battery.

2. The improved neurological testing apparatus of claim 1 further comprising:
    an eye examination lens for examining the fundus (retina) of the patient,
    the lens being mounted in a hole in the body housing structure extending through the body housing structure from the rear surface through to the front surface and being aligned with and located above the light open to the cavity in the body housing structure,
    the lens extending from the rear surface and opened to a hole or opening in the front surface; and
    a mirror or prism positioned in the cavity between the light and the lens for redirecting the emitted light through the hole in the vision chart label on the front surface, the hole being aligned with the field of view of the lens.

3. The improved neurological testing apparatus of claim 1 wherein one end has an integral disk having a red side and an opposite white side to use in field of vision determination.

4. The improved neurological testing apparatus of claim 3 wherein an opposite end of the body housing structure relative to the end with the integral opposite the disk includes a cavity or slot or slotted cavity between the front and rear surface for holding instruction cards or patient information cards.

5. The improved neurological testing apparatus of claim 1 wherein the smell testing substances and the taste testing substances all lie on the same front or rear surface.

6. The improved neurological testing apparatus of claim 5 wherein each vision chart lies on a front or rear surface opposite to the taste or smell testing surface.

7. The improved neurological testing apparatus of claim 1 wherein each separate specific smell testing substance is spaced from each other and is formed in stacked layers or strips, each layer or strip being covered or sealed by a re-sealable cover.

8. The improved neurological testing apparatus of claim 7 wherein the stacked layers or strips have a specific smell substance attached to the underside of the layer or strip which is exposed upon opening of the re-sealable cover.

9. The improved neurological testing apparatus of claim 7 wherein the stacked layers or strips have a specific smell substance attached to the top side of the layer or strip which is exposed upon opening of the re-sealable cover.

10. The improved neurological testing apparatus of claim 1 wherein each separate specific taste testing substance is spaced from each other and is formed in stack layers or strips, each layer or strip being covered or sealed by a re-sealable cover.

11. The improved neurological testing apparatus of claim 10 wherein the stacked layers or strips have a specific taste substance attached to the underside of the layer or strip which is exposed upon opening of the re-sealable cover.

12. The improved neurological testing apparatus of claim 10 wherein the stacked layers or strips have a specific taste substance attached to the top side of the layer or strip which is exposed upon opening of the re-sealable cover.

13. The improved neurological testing apparatus of claim 1 further comprising:
    a plurality of cotton tipped swabs; and
    wherein the body housing structure further comprises one or more recessed swab holders molded or otherwise formed in the body housing structure for holding one or more removable cotton tipped swabs.

14. The improved neurological testing apparatus of claim 1 further comprising an edge surface between the front and rear surface, wherein a portion of the edge surface comprises a measuring scale.

* * * * *